United States Patent
Poenie et al.

(10) Patent No.: US 8,329,449 B2
(45) Date of Patent: Dec. 11, 2012

(54) IMMOBILIZED RESINS FOR ALGAL OIL EXTRACTION

(75) Inventors: Martin Poenie, Austin, TX (US); Jessica Jones, Austin, TX (US); James Beach, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 279 days.

(21) Appl. No.: 12/903,996

(22) Filed: Oct. 13, 2010

(65) Prior Publication Data

US 2011/0083360 A1  Apr. 14, 2011

Related U.S. Application Data

(60) Provisional application No. 61/251,116, filed on Oct. 13, 2009.

(51) Int. Cl.
*C12N 1/00* (2006.01)
(52) U.S. Cl. .......... 435/257.3; 435/257.1; 554/175
(58) Field of Classification Search .......... 435/257.1, 435/257.3; 554/175
See application file for complete search history.

(56) References Cited

U.S. PATENT DOCUMENTS

| | | | | |
|---|---|---|---|---|
| 4,341,038 | A | | 7/1982 | Bloch et al. |
| 5,539,133 | A | * | 7/1996 | Kohn et al. ............... 554/20 |
| 6,166,231 | A | * | 12/2000 | Hoeksema ............... 554/12 |
| 6,805,800 | B1 | | 10/2004 | Keating |
| 7,905,930 | B2 | | 3/2011 | Oyler |
| 2008/0160593 | A1 | * | 7/2008 | Oyler .................. 435/166 |
| 2008/0226740 | A1 | * | 9/2008 | Chen et al. ............ 424/499 |
| 2009/0234146 | A1 | * | 9/2009 | Cooney et al. ......... 554/174 |

OTHER PUBLICATIONS

International Search Report and Written Opinion for PCT/US2010/052549, dated Oct. 13, 2009, 7 pages.

* cited by examiner

*Primary Examiner* — Deborah D Carr
(74) *Attorney, Agent, or Firm* — Edwin S. Flores; Chainey P. Singleton; Chalker Flores, LLP

(57) ABSTRACT

A reverse phase extraction method for the recovery of triglycerides from aqueous slurries of algae is described herein. The present invention discloses the use of immobilized anion exchange and lipid binding resins. As the algae flows past the resin, triglycerides adhere while the bulk of the algae flows through. The lipids, useful for generating biofuels are then are eluted off the resin. The method of the present invention does not require prior drying of the algae, is inexpensive, and does not destroy the algal biomass which can be used for other purposes.

29 Claims, 8 Drawing Sheets

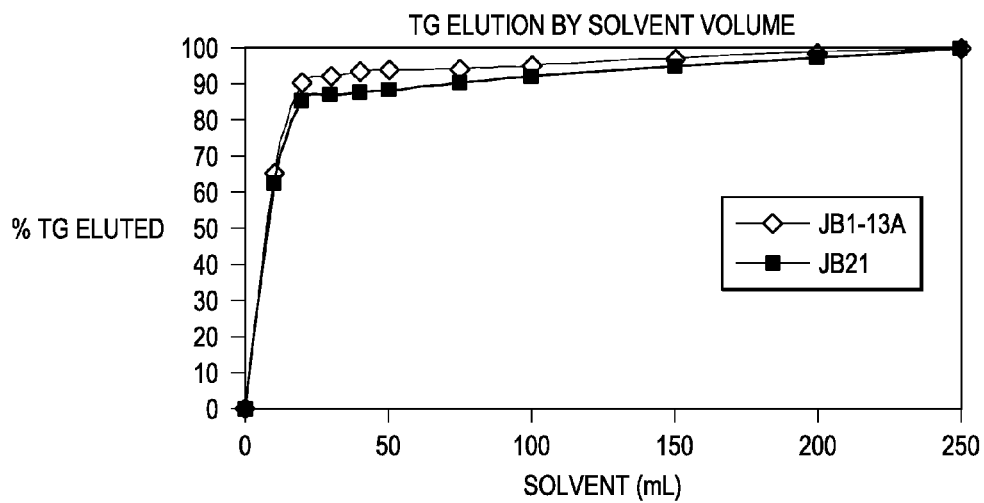
FIG. 9
FIG. 10
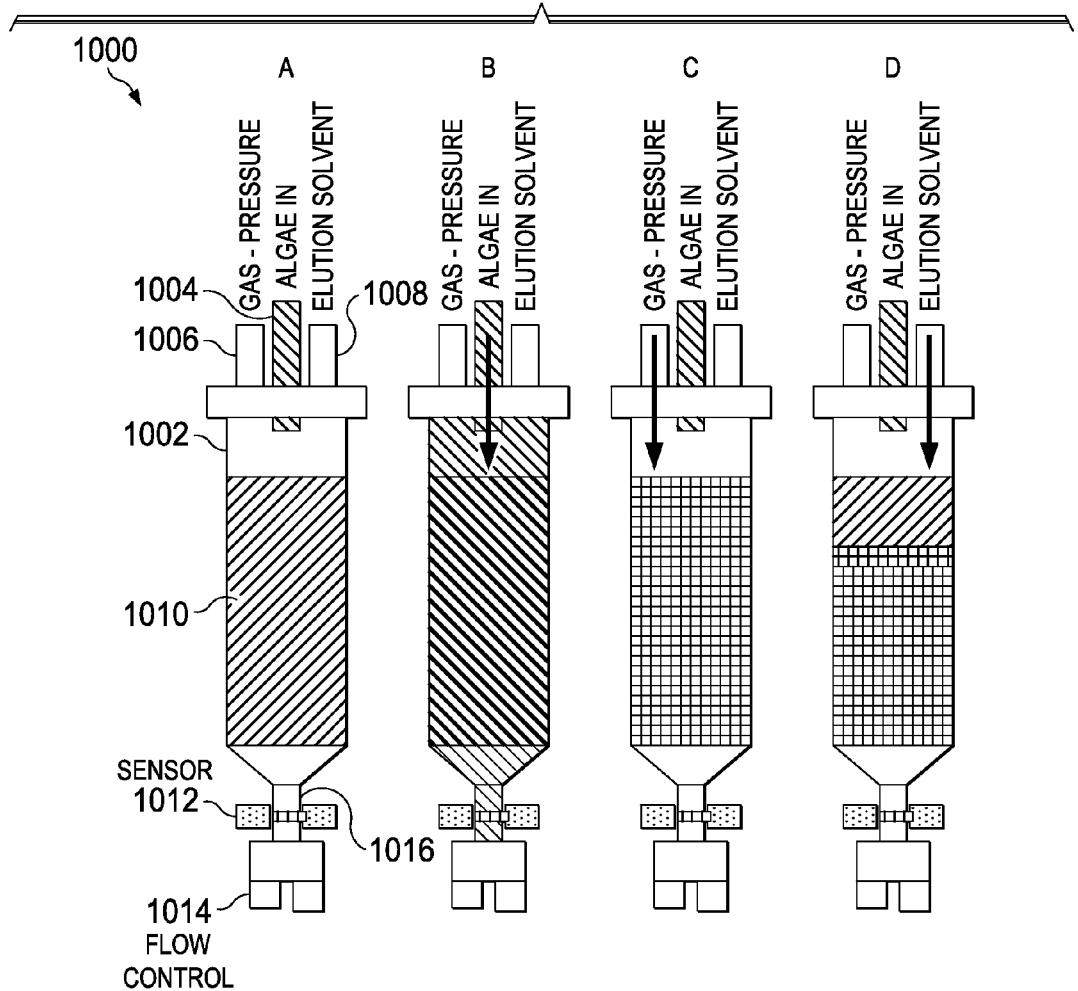

IMMOBILIZED RESINS FOR ALGAL OIL EXTRACTION

CROSS-REFERENCE TO RELATED APPLICATIONS

This U.S. patent application claims priority from U.S. Provisional Patent Application Ser. No. 61/251,116, filed on Oct. 13, 2009, the entire contents of which are incorporated herein by reference.

TECHNICAL FIELD OF THE INVENTION

The present invention relates in general to the field of algal oil recovery, and more particularly, to the design and development of a novel reverse phase method for the extraction of algal triglycerides and lipids used in biofuel production.

STATEMENT OF FEDERALLY FUNDED RESEARCH

None.

INCORPORATION-BY-REFERENCE OF MATERIALS FILED ON COMPACT DISC

None.

REFERENCE TO A SEQUENCE LISTING

None.

BACKGROUND OF THE INVENTION

Without limiting the scope of the invention, its background is described in connection with the extraction of commercially important compounds including lipids from algal cultures.

U.S. Pat. No. 4,341,038 issued to Bloch et al. (1982) relates to the cultivation and harvesting of halophile algae, especially of the *Dunaliella* type, and to a process for the recovery from such algae of oil products useful as a source of energy, specifically as fuel or as a chemical feedstock. According to the '038 patent oil products and a high nitrogen content residue are obtained by growing halophilic algae in saline solution, harvesting an algae-salt water slurry, solvent extracting said slurry, and recovering the product and residue. Use of a growth promoting enzyme, salt concentration gradients for harvesting, and water insoluble solvents at elevated temperatures are preferred.

U.S. Pat. No. 6,805,800 issued to Keating (2004) describes a method of recovering fat soluble compounds, including but not restricted to pigments such as beta-carotene, from solutions, including but not restricted to those solutions containing microalgal cells. According to the Keating patent, the method comprises passing a solution containing a fat soluble compound is passed through a fluidized bed of crystalline metallic ore particles, such as magnetite, allowing the fat soluble compound to bind to the particles to form a complex. The fat soluble compound is released from the complex by passing a wash solution through the fluidized bed and is subsequently collected in the solution.

SUMMARY OF THE INVENTION

The present invention describes two novel approaches for extraction of triglycerides, and other lipids from algal cultures. The method described in the present invention includes the use of immobilized anion exchange to recover and convert the fatty acid components of triglycerides, diglycerides and polar lipids such as glyerophospholipids to fatty acid methyl esters. The fatty acid methyl esters are used to produce "biodiesels" by transesterification (catalyzed by either an acid or a base). Further the present invention also describes the use of lipid binding resins to obtain triglycerides and other lipids.

In one embodiment the present invention is a method of extracting one or more lipid components from an aqueous algal suspension or slurry comprising the steps of: (i) saturating an anion-exchange resin contained in a column or any suitable container with the algal suspension or slurry, (ii) removing any excess water of liquids from the column or the container, by applying a gas pressure, applying a vacuum, air drying the column or the container, or using a combination of other drying techniques, (iii) flowing an eluent through the algae saturated column or the container to elute the algae off the column, and (iv) collecting the eluted algae in a receiver connected to the column or the container, wherein the eluted algae comprises the one or more lipid components and the eluent. The method of the present invention further comprises the steps of: applying a temperature, a gas pressure, a vacuum, air drying the column or the container or using a combination of other drying techniques to remove any excess eluent from the column or the container, recycling the eluent solution to elute the algae off the column, and repeating the steps of saturating and extracting the one or more lipid components from a subsequent batch of aqueous algal suspension or slurry. In one aspect of the method of the present invention the eluted algae in the receiver is converted to a Fatty Acid Methyl Esters (FAMEs) or a biodiesel.

In another aspect the anion-exchange resins comprise a cross-linked polymer backbone with functional groups comprising quarternary ammonium salts, tertiary amines, secondary amines, primary amines, organometallic complexes, any charged species manufactured by corona discharge or plasma ion embedment or any combinations thereof with a replaceable cation. The polymer backbone is a selected from the group consisting of styrene, styrene-divinyl benzene, polystyrene, formophenolic, acrylic-divinyl benzene, methacryl-divinyl benzene, functionalized styrene monomers functionalized acrylic monomers, functionalized methacrylic monomers, acrylamides, methacrylamides, epoxy, acrylic monomers, polypropylene or functionalized polyvinyl chloride polymers. In one aspect the anion exchange resin is an electrostatically charged polyethylene. In a specific aspect the polymer backbone is divinyl benzene and the functional group is quarternary ammonium salt. In yet another aspect the algae are selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis, Neochloris oleoabundans*, and *Pleurochysis*. In specific aspects of the method the eluent comprises methanol acidified with sulfuric acid the algae is a *Chlorella* or a *Nanochloropsis*.

In another embodiment the present invention describes a method of extracting one or more lipid components from an aqueous algal suspension or slurry of *Chlorella, Nanochloropsis* or both using an anion exchange resin column or a container, wherein the anion exchange resin comprises a divinyl benzene or other or other crosslinked polymer backbones with an attached quarternary ammonium salt functional group comprising the steps of: saturating the anion exchange column or the container with the *Chlorella* or *Nanochloropsis* or both, wherein the saturation of the column or the container is determined by a presence of the *Chlorella, Nanochloropsis* or both in a column effluent detected by an optical sensor attached to the base of the column or the container, removing any excess water of liquids from the column or the container, by applying a gas pressure, applying a vacuum, air drying the column or the container, or using a combination of other drying techniques, flowing an eluent comprising methanol acidified with sulfuric acid through the algae saturated column or the container to elute the algae off, and collecting the eluted *Chlorella, Nanochloropsis* or both in a receiver connected to the column the column, wherein the eluted algae comprises the one or more lipid components and the eluent. The method further comprises the steps of: applying a gas pressure, a vacuum, a temperature, air drying the column or the container, or using a combination of other drying techniques to remove any excess eluent from the column or the container and repeating the steps of saturating and extracting the one or more lipid components from a subsequent batch of aqueous algal suspension or slurry of *Chlorella, Nanochloropsis* or both. The elution solution comprising methanol acidified with sulfuric acid can be used more than once with some additional sulfuric acid added for each cycle of elution. Since the amount of lipid transesterified from a single elution is relatively small, the methanol would not be used up, thus making the elution solution suitable for at least one to a few cycles of elution. Reuse of the methanol/sulfuric acid makes the method of the present invention more economical. In one aspect the anion exchange resin is an electrostatically charged polyethylene. The *Chlorella, Nanochloropsis* algae or both eluted by the method of the present invention is converted to a Fatty Acid Methyl Esters (FAMEs) or a biodiesel.

In yet another embodiment the present invention discloses a method of extracting one or more lipid components from an aqueous algal suspension or slurry comprising the steps of: saturating a lipid binding column comprising a hydrophobic resin or a container with the algae, stopping the flow of the algae at the saturation point of the column or the container, applying a gas pressure or a vacuum to the column or the container to remove any residual algae from the column or the container, passing a solvent (selected from the group consisting of hexane or other alkanes, chloroform or other halogenated solvents, ethers such as diethyl ether, ketones such as acetone, and other aromatic solvents such as benzene and toluene) through the column or the container to extract the bound one or more lipid components and the oils, collecting the solvent comprising the dissolved one or more lipid components and the oil in a separate receiver; and removing the solvent to obtain a concentrate comprising the one or more lipid components and the oil. The method of the present invention further comprises the steps of analyzing the solvent comprising the dissolved one or more lipid components by one or more analytical techniques selected from the group consisting of high pressure liquid chromatography (HPLC), gas chromatography (GC), fluorescence, thin-layer chromatography (TLC), and other chromatographic methods removing any excess water of liquids from the column or the container by applying a gas pressure, applying a vacuum, air drying the column or the container, or using a combination of other drying techniques, repeating the steps of saturating and extracting the one or more lipid components from a subsequent batch of aqueous algal suspension or slurry, and converting the concentrated lipid components and oil in the receiver to Fatty Acid Methyl Esters (FAMEs) or a biodiesel by transesterification using either an acid or a base as a catalyst.

In one aspect of the method the lipid binding resin comprises a polymer backbone is a selected from the group consisting of styrene, divinyl benzene, styrene-divinyl benzene, polystyrene, formophenolic, acrylic-divinyl benzene, methacryl-divinyl benzene, functionalized styrene monomers functionalized acrylic monomers, functionalized methacrylic monomers, acrylamides, methacrylamides, epoxy, and acrylic monomers, wherein one or more copolymerizing monomers with various hydrophilic or hydrophobic functional groups are attached to the polymer backbone. In yet another aspect the algae are selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis, Neochloris oleoabundans*, and *Pleurochysis*. In an other aspect the solvent comprises acetone, heptane, hexane, pentane, benzene, toluene, tetrahydrofuran, diethyl ether, ethyl acetate or mixtures thereof. In yet another aspect the algae is a *Chlorella* or a *Nanochloropsis*. In specific aspects the polymer backbone is a crosslinked divinyl benzene, or other crosslinked monomers wherein the polymer backbone is at least 2% cross-linked and the organic solvent may be a polar solvent, for e.g. acetone, or a non-polar organic solvent like hexane.

In one embodiment the present invention describes a method of extracting one or more lipid components from an aqueous algal suspension or slurry of *Chlorella, Nanochloropsis* or both comprising the steps of: (i) saturating a lipid binding resin column or a container comprising a crosslinked divinyl benzene backbone with the suspension or slurry of the *Chlorella* or the *Nanochloropsis*, (ii) applying a gas pressure, temperature and/or a vacuum to the column to remove any residual algae from the column or the container, (iii) passing hexane or other non-polar organic solvent through the column or the container to extract the bound one or more lipid components and the oils, (iv) collecting the hexane or the non-polar organic solvent comprising the dissolved one or more lipid components and the oil in a separate receiver and (v) removing the hexane or the non-polar organic solvent to obtain a concentrate comprising the one or more lipid components and the oil. In one aspect the extraction method further comprises the step of analyzing the hexane or the non-polar organic solvent comprising the dissolved one or more lipid components by one or more analytical techniques selected from the group consisting of high pressure liquid chromatography (HPLC), gas chromatography (GC), fluorescence, thin-layer chromatography (TLC), and other chromatographic methods.

In further steps the method of the present invention entails removing any excess hexane from the column by applying a temperature, a gas pressure, a vacuum, air drying the column or the container, or using a combination of other drying techniques and repeating the steps of saturating and extracting the one or more lipid components from a subsequent batch of aqueous algal suspension or slurry of *Chlorella, Nanochloropsis* or both. The method of the present invention further comprises the step of converting the concentrated lipid components and oil in the receiver to Fatty Acid Methyl Esters (FAMEs) or a biodiesel.

BRIEF DESCRIPTION OF THE DRAWINGS

For a more complete understanding of the features and advantages of the present invention, reference is now made to the detailed description of the invention along with the accompanying figures and in which:

(FIG. 2A) a typical HPLC chromatogram from *Nanochloropsis*, (FIG. 2B) shows a HPLC trace of material present in the methanol/sulfuric acid/algae mixture eluted from the anion exchange resin. The large peak in (FIG. 2B) is shifted slightly from the TG peak seen in (FIG. 2A) and corresponds to FAMEs, (FIG. 2C) shows a rerun trace of the HPLC in (FIG. 2B) spiked with a TG standard;

(FIG. 4A) shows how virtually all the algae flows through small test columns loaded with a lipid-binding resin, (FIG. 4B) shows the elution of only a small amount of lipid from the column in the acetone wash, (FIG. 4C) shows the elution of a much larger amount of triglyceride, along with long chain hydrocarbons and diglyceride from the column;

(FIG. 5A) untreated control algae, (FIG. 5B) algae after passing through a hydrophobic resin column;

FIG. 9 is a graph showing the elution efficiency of lipid-binding resins. Algae was passed over the column allowing it to accumulate oil on the resin. Subsequently, solvent was passed over the resin and collected in 10 ml aliquots, which were then analyzed for oil content by HPLC. The graph shows that the oil is readily eluted from the column; and FIGS. 10A-10D show the use of lipid-binding resin for oil extraction as described in an embodiment of the present invention.

DETAILED DESCRIPTION OF THE INVENTION

Figure 1:
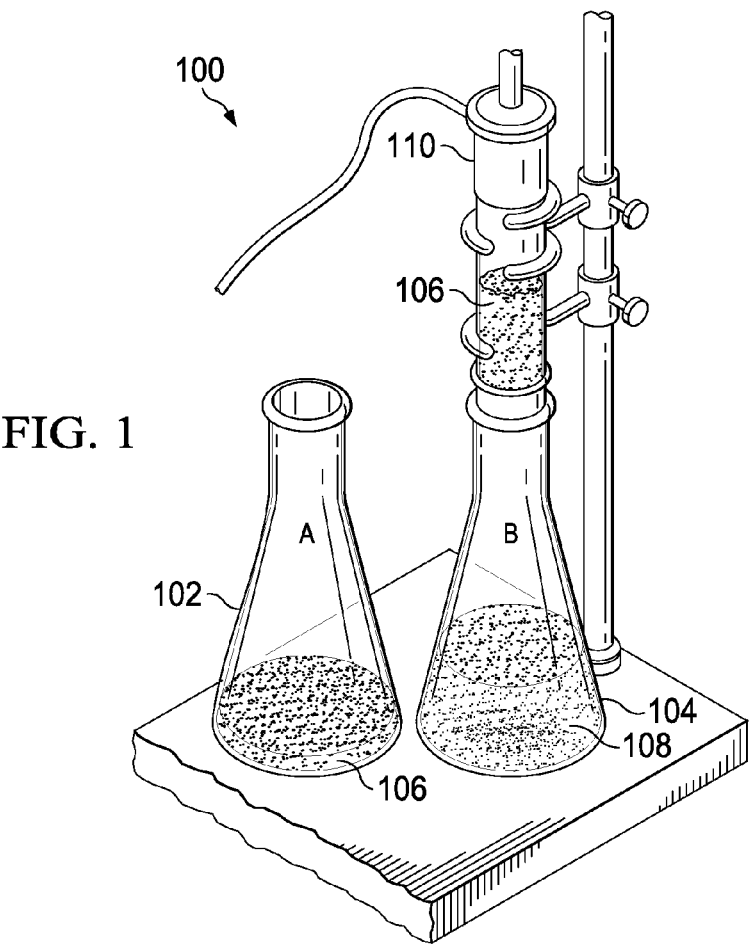
FIG. 1 is a study showing the ability of an anion exchange resin to collect algae. 40 ml of resin was able to accumulate the algae from more than 1 liter of half-percent algae suspension. The starting algae suspension is labeled "A". As can be seen, the flow through, labeled "B" through from the column is completely clear.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "algae" represents a large, heterogeneous group of primitive photosynthetic organisms which occur throughout all types of aquatic habitats and moist terrestrial environments. Nadakavukaren et al., Botany. *An Introduction to Plant Biology*, 324-325, (1985). The term "algae" as described herein is intended to include the species selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis*.

The term "ion exchange resin" as used herein refers to a solid organic material having a matrix with fixed ions (i.e., chemically bound functional groups) and oppositely charged mobile counter ions which can be exchanged reversibly with ions of like charge from a surrounding liquid medium. The mobile counter ions within the resin provide ionic, electrical conductivity, and correspondingly electrically driven mass transport, within the resin which is largely fixed and substantially independent of the surrounding solution.

As used herein, the term "hydrophobic resin" refers to column resins that are hydrophobic. For example, the term is intended to encompass such packing materials as C18 (indicated as being hydrophobic by Margois-Nunno and Horowitz, PCT Publ. No. WO 95/00631, page 11). "Hydrophobic resins" also includes resin having a equilibrium moisture content of 0.5% or lower, and is specifically exemplified by a variety of polyethylene, polypropylene, polyester and ethylene-vinyl acetate copolymers that may be used alone or in admixture.

The terms "esterification" or "transesterification" as used herein refer to processes by which an acid group is added, hydrolyzed, repositioned or replaced on one or more components of the substrate. The acid group can be derived from a fat or oil which is part of the initial substrate or from a free fatty acid or ester that has been added to the deodorized substrate or purification media-processed substrate.

The term "esterification" includes the process in which R, R' or R" on a glyceride is converted from an alcoholic group (OH) to a fatty acid group given by —OC(=O)R'". The fatty acid group which replaces the alcoholic group can come from the same or different glyceride or from a free fatty acid or ester that has been added to the deodorized substrate or the purification media-processed substrate. A non-limiting example of "esterification" includes reaction of a free fatty acid with an alcohol. Esterification also includes processes pertaining to the manufacture of biodiesel, such as discussed in U.S. Pat. Nos. 5,578,090, 5,713,965, and 6,398,707.

The term "transesterification" as used herein includes the process in which R, R' or R" on a glyceride is a first fatty acid group given by —OC(=O)R'", and the first fatty acid group is replaced by a second, different fatty acid group. The second fatty acid group which replaces the first fatty acid group can come from the same or different fat or oil present in the initial substrate. The second fatty acid can also come from a free fatty acid or ester added to the deodorized substrate or the purification media-processed substrate. A non-limiting example of transesterification includes reaction of a fat or oil with an alcohol (e.g., methanol) or with an ester.

The term "biodiesel" as used herein refers to a vegetable oil- or animal fat-based diesel fuel consisting of long-chain alkyl (methyl, propyl or ethyl) esters. Biodiesel is typically made by chemically reacting lipids (e.g., vegetable oil, animal fat (tallow)) with an alcohol. The term "biodiesel" includes lower alkyl esters of fatty acid groups found on animal or vegetable glycosides. Lower alkyl esters include methyl ester, ethyl ester, n-propyl ester, and isopropyl ester.

The present invention describes a reverse phase extraction method for the recovery of triglycerides and other lipids from aqueous slurries of algae. As the algae flows past the resin, triglycerides adhere while the bulk of the algae flow through. The lipids, useful for generating befouls are then are eluted off the resin.

Current technologies for algal lipid extraction involve solvent extraction or supercritical methanol. These methods are more expensive and destroy the algae biomass for other uses. The method of the present invention does not require prior drying of the algae and is compatible with the existing lying technologies.

While algae make oil there is no simple and economical method for extracting the oil directly from an aqueous slurry. Drying algae is usually needed for efficient solvent extraction and the biomass is exposed to toxic solvents. Other methods such as are critical point $CO_2$ or critical point methanol are expensive. The method of the present invention combined with a flow through lysis allows the algae to simply flow past the resin which then can be eluted with solvents to retrieve the collected oil. The solvent can then be recycled. The use of solvents is minimized and the solvents do not contact the algae directly thus, making the method of the present invention both simple and economical.

Although there is a great potential for the use of algae as a source of biofuels a number of technological developments are needed before recovery of oil will be economical. Key issues deal with the large amounts of water involved in growing algae which typically grows t$_o$ concentrations of less than one percent. Harvesting and dewatering algae from low-density cultures has been achieved but this often yields a paste whose physical properties make subsequent processing difficult. For example, these pastes still contain considerable amounts of water that prevent direct mixing with organic solvents and they do not flow through extraction equipment.

The present inventors have developed several new approaches to algae dewatering and oil extraction using resin surfaces that bind to either algae or directly to algae lipids. The first of these approaches utilizes ion exchange resins that bind algae as water flows through the matrix. This is a solution that, at present, applies primarily to fresh water algae since the high salt content of sea water prevents algae from binding to the resin. Once bound, the only water that remains is in what is known as the void volume, the spaces between the resin particles. The present inventors have demonstrated a 200-fold concentration of the algae. Furthermore, the residual water can be removed by gas pressure or vacuum or other methods. Once the algae has been bound it can be eluted by several methods including acidification of the media to neutralize the charge on the algae or with base or salt that provide ions that compete with for binding sites on the resin.

Use of Anion Exchange resins for biodiesel production: The phenomenon of algae concentration on a resin makes these resins suitable for use in the generation of biofuels. The standard approach for making biodiesel involves a transesterification reaction using an alcohol and an acid or base catalyst. Although one could directly mix an algal slurry with methanol and acid to get biodiesel, one would have to add enough sulfuric acid to dehydrate the mixture which would be cost prohibitive. However, since dewatering is nearly complete on the resin, it is possible to simultaneously elute the algae off the resin and convert all the saponifiable lipids to fatty acid methyl esters in one step using methanol and low concentrations of sulfuric acid (acid-catalyzed) or one or more bases (base-catalyzed) selected from sodium hydroxide, potassium hydroxide, sodium methoxide or ethoxide and combinations or modifications thereof.

Removal of water makes it economical to attempt direct conversion of algae lipids to fatty acid methyl esters (FAMEs), which are sold as biodiesel. One way to convert the lipids in algae to FAMEs is to mix algae with methanol in the presence of a catalyst, which can be either an acid (sulfuric acid) or a base (sodium hydroxide, potassium hydroxide, sodium methoxide or ethoxide). Studies conducted by the present inventors have demonstrated that methanol/sulfuric acid will elute quantitatively algae off the anion exchange column regenerating the resin for another cycle of collecting algae. Alternatively, the present inventors have also shown that sodium hydroxide in methanol can also elute algae from the column, thus providing an alternative method for making FAMEs. At the same time, the mixture of algae, methanol and sulfuric acid coming off the column reacts to convert all the saponifiable lipids including triglycerides, phospholipids and glycolipids to FAMEs.

Figure 2A:
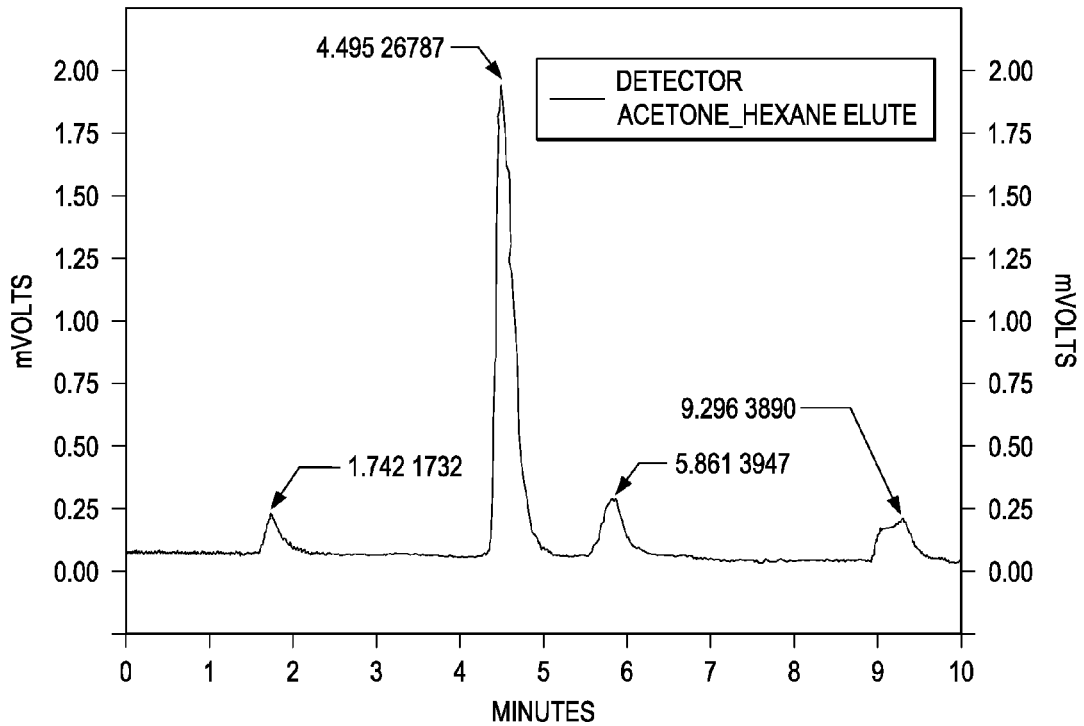
FIGS. 2A-2C show FAME production from algae using an anion exchange column.
Figure 2B:
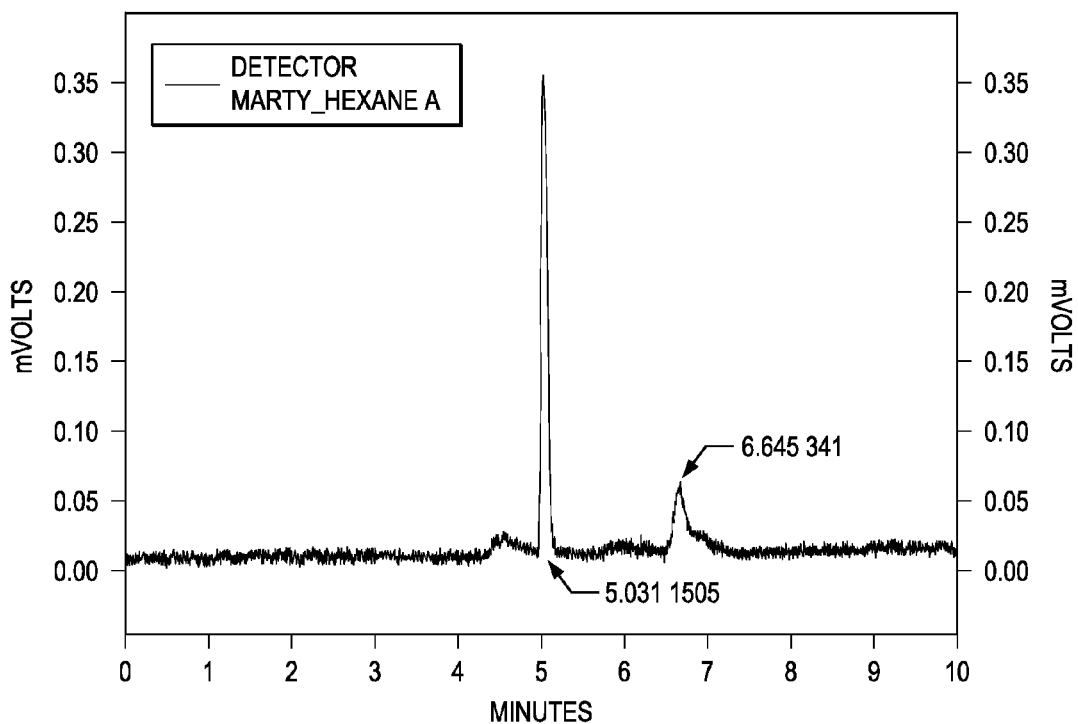
Figure 2C:
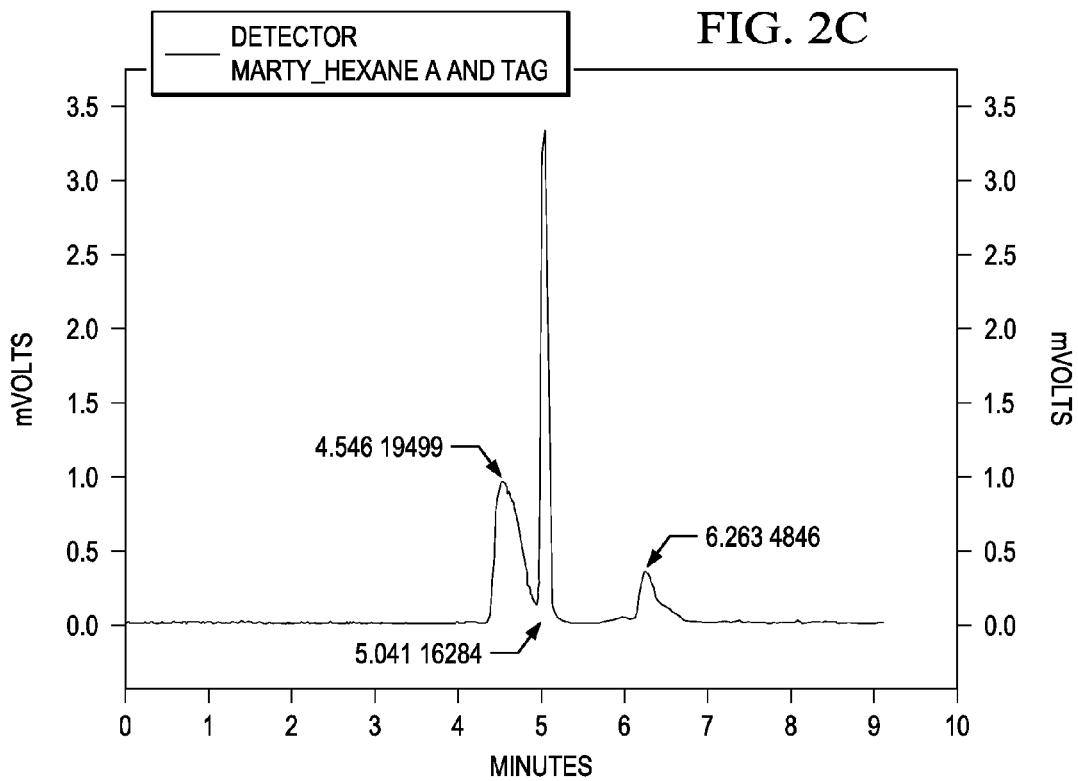

The inventors concentrated algae on an ion exchange resin as shown in FIG. 1. FIG. 1 is a study 100 showing the ability of an anion exchange resin 110 to collect algae. 40 ml of resin was able to accumulate the algae from more than 1 liter of half-percent algae suspension 106. The starting algae suspension 106 is labeled "A" in a flask 102. As can be seen, the flow through 108, labeled "B" through from the column 110 is completely clear. Residual water was expelled with air and then the resin was eluted with a mixture of methanol and 1% sulfuric acid. The next day the mixture was extracted with organic solvents using water to split away the organic layer, and the extract was analyzed by HPLC (FIG. 2). The inventors found that essentially all the triglyceride normally present in the algae (FIG. 2A) were apparently converted to FAMEs (FIG. 2B). FAMEs run slightly slower than triglycerides on the normal phase HPLC column and comparison with methyl laurate showed that the new peak coincided with that of the methyl laurate standard. To verify this, the inventors repeated the analysis but with added triglyceride (FIG. 2C). The results showed a triglyceride peak running distinctly ahead of the FAME peak in the sample.

The observed ability of anion exchange resins to bind algae enables applications for dewatering algae and extraction of oil. These resins bind and accumulate algae present in algal suspensions as the water flows through them. Once the resins are saturated with algae, residual water can be removed.

There are other possible applications for anion exchange resins. One could imagine using belts with the same anion exchange properties used to harvest algae from ponds. The belt would bridge between the pond and the shore collecting the algae from the pond and then eluted onshore. As the belt leaves the water, residual water would drain away and air drying could follow. One could also envision floating containers packed with resin that reside in the pond to collect algae and are then removed and eluted or otherwise processed. In either case, it avoids pumping large amounts of water.

As mentioned previously, the resin is readily eluted and regenerated with a mixture of methanol and sulfuric acid and one step; one can elute and generate FAMEs. Normally, the sulfuric acids need be present only in catalytic amounts to generate FAMEs. Somewhat higher amounts of acid are needed to elute the algae. However, one of the current methods used to concentrate algae is to treat with base and then acid to effect flocculation. These methods also involve introducing acids and bases into the process so that should not be a fatal objection. Furthermore, it is possible that the sulfuric acid methanol can be reused to elute resins more than one time thus concentrating the FAMEs and minimizing the use of methanol and sulfuric acid.

Another possibility for resin elution is the use of $CO_2$ dissolved in water under pressure. When $CO_2$ is dissolved in water, it forms carbonic acid and, depending on concentration, can reduce the pH to levels low enough to protonate carboxyl groups. This will neutralize the charge on the algae, releasing it from the resin.

Ion exchange resins have much potential for harvesting and processing algae it could have immediate benefits in achieving the required deliverables. To measure the algae-binding capacity of the resin the inventors prepared a column with 5.0 g of Amberlite CG-400, strongly basic quaternary ammonium ion type of resin. A suspension of Chlorella containing 9.9 mg algae (dry weight) 10 ml suspension was passed over the column. Saturation was determined by appearance of algae in the flowthrough. 190 ml of the algal suspension was required to saturate the column Thus, the total amount of algae used was 0.19 g per 5.0 g of resin (or 0.038 g algae/g resin or 40 g algae/kg resin).

Saturation point is a function of the flow rate through the column and the concentration of the algae suspension. It depends on a number of factors including the size of the column and pressure applied. Obviously time is reduced if the starting concentration of algae is higher. Assuming, the inventors processed 60 gallons of 0.5% algae suspension at a flow rate of 1 gallon per minute of, it would take 1 hour to saturate the column and this would permit 8-10 cycles a day at 500 grams per cycle. If the algae concentration were only ⅕ as concentrated, it would still give two cycles a day and more than 1 liter of oil.

Since elution occurs the instant the methanol/sulfuric acid contacts the resin, elution time is minimal. The elution volume would be roughly ⅓ to ½ the resin volume. Since 1 Kg of resin is less than 1 liter, we estimate that 10 kg of resin would occupy 7-8 liters volume and the elution volume would be roughly 4-5 liters of methanol sulfuric acid. Ultimately this would contain 20% oil. The methanol/sulfuric acid eluent is passed through the column to elute more than one batch of algae. The oil that forms (FAMEs) float to the surface after time allowing them to either be drained off or extracted. Ultimately the reaction mixture will accumulate glycerol and other algae byproducts that will need to be separated.

Figure 3:
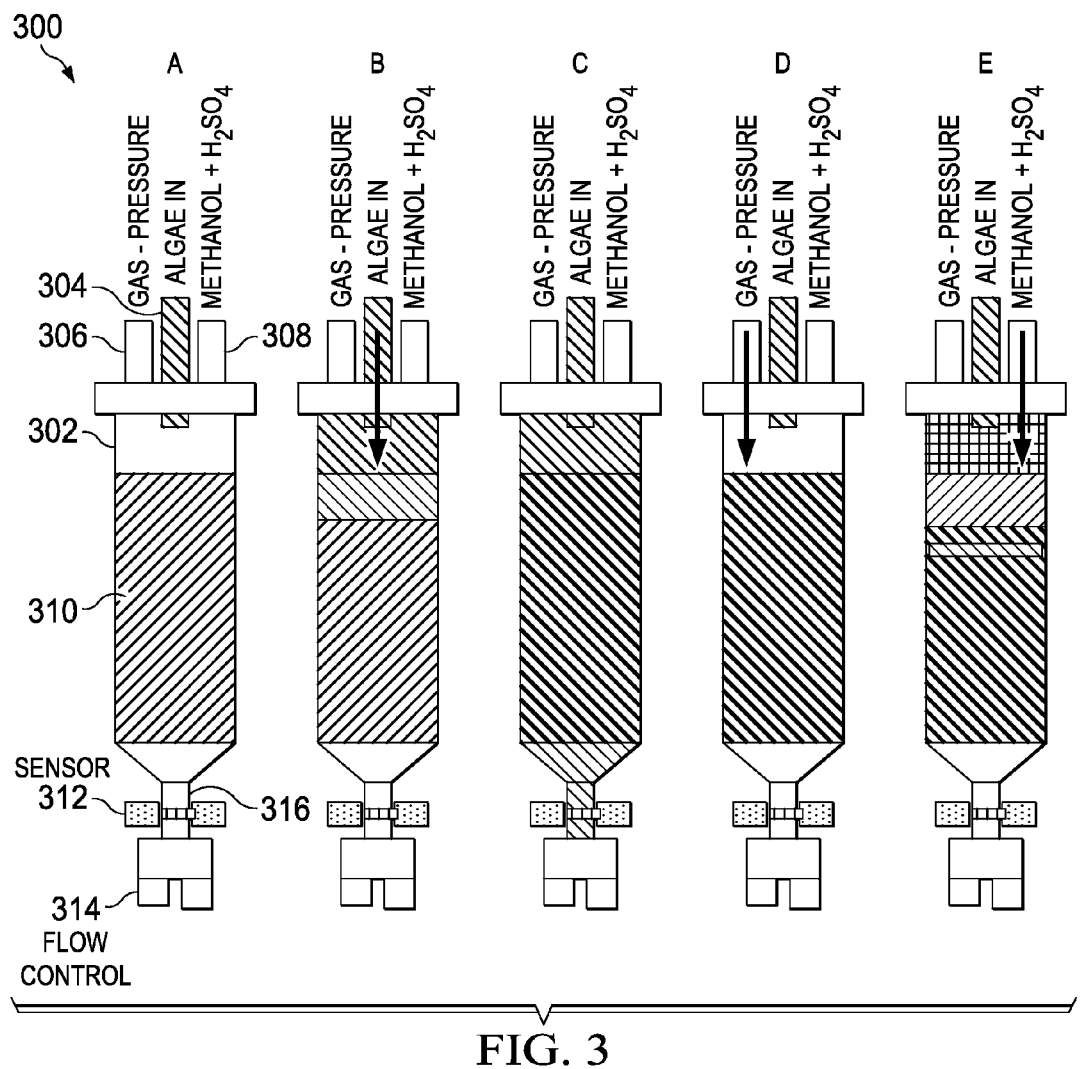
FIGS. 3A-3E are a schematic showing the application of an anion exchange resin in oil production as described in an embodiment of the present invention.

The inventors describe a sequence of steps in FIG. 3 that shows the process 300 of the present invention. Algae 304 would flow through the column 302. Initially the effluent coming out of the column 302 is completely clear but when the column becomes saturated algae will begin to flow through the resin bed 310. The inventors show an optical detector 312 for an automated system to detect the saturation point although in initial testing overflow would be determined visually. Once the column 302 is saturated either gas pressure or vacuum would be used (306) to remove residual water. Subsequently a solution of methanol/sulfuric acid (308) is pumped through the resin 310 which immediately elutes the algae. This is collected in a separate container using the flow control valve 314. Once the algae are eluted, either gas pressure or vacuum (306) is used once again to remove the residual reagents. Then the cycle starts over again.

The basic anion exchange resin column 302 with resin bed 310 is shown in FIG. 3A. The system has an optical sensor 312 at the effluent nozzle 316 to detect when the column 302 is saturated and algae starts coming through. There are three inputs to the column, one for algae flow 304 into the resin bed 310, one for a gas 306 that pushes out remaining water when the column 310 is saturated and one for methanol/sulfuric acid 308 used to elute the algae and convert all fatty acids into fatty acid methyl esters (FAMEs). As shown in FIG. 3B the cycle begins with flowing algae suspension into the column 302. This loads the column 302 with algae. When the column 302 is saturated, algae will begin to leak off the column 302 and is detected by the optical sensor 312 at the base (FIG. 3C). This optical sensor 312 will be a flow through sensor commonly used in column chromatography. Once the sensor detects algae flowing past the resin bed 310, the algae flow is stopped and gas pressure is used to force the remaining water out of the resin bed 310. The flow through sensor 312 would detect this also (FIG. 3D). As seen in FIG. 3E once water is removed from the resin 310, a solution of methanol containing small amounts of sulfuric acid would be introduced into the column through inlet 308. This will elute the algae off the column 302 and the eluted methanol/algae/sulfuric acid solution will generate (FAMEs). The flow control valve 314 switches the output to a separate receiver. Gas pressure is used to force the remaining methanol/sulfuric acid mixture off the resin. The cycle then starts over.

Direct oil extraction with lipid binding resins: A second approach for obtaining oil from algae using lipid binding resins has been developed by the present inventors and described in this disclosure. The resins described herein are based on crosslinked hydrophobic polymer networks in which copolymerizing monomers with various functional groups were added. These substituents were varied so as to give the polymers various hydrophobic or hydrophilic moieties and/or they were imprinted with lipids, especially triglycerides during the synthesis. Lipid imprinted polymers were subsequently washed and extracted thoroughly such that no further seepage of oil was detectable by HPLC. A key to the polymers is shown in Table 1. All polymerizations were carried out in bulk except for polymers JB1-14A, B and C which were polymerized as a suspension in water.

Testing of these polymers was conducted initially using an emulsion of triglycerides that contained Nile Red as a tracking dye. This allowed a rapid screening of the various polymers both visually and spectrophotometrically. Visually one could see that virtually all the Nile Red was retained until the column was eluted with organic solvents. Spectrophotometry confirmed that for a number of the resins, 90-95% of the dye bound to the column (along with triglycerides). Follow-up studies using HPLC confirmed that triglycerides were bound tightly to the column. Using this simple and rapid approach, the inventors screened a relatively large number of polymers for their potential usefulness.

Figure 4A:
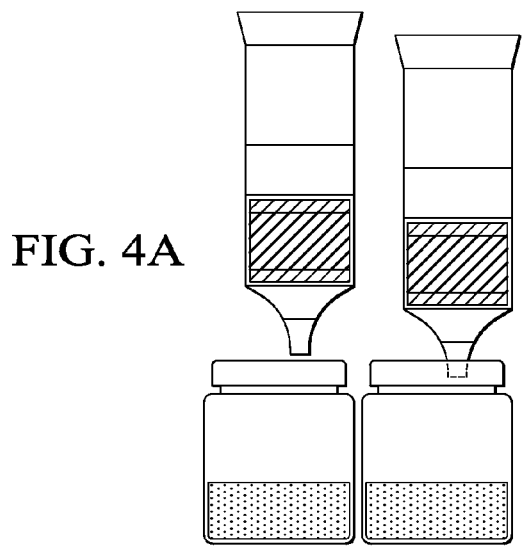
FIGS. 4A-4C show the results of a lipid binding column study.
Figures 4B, 4C:
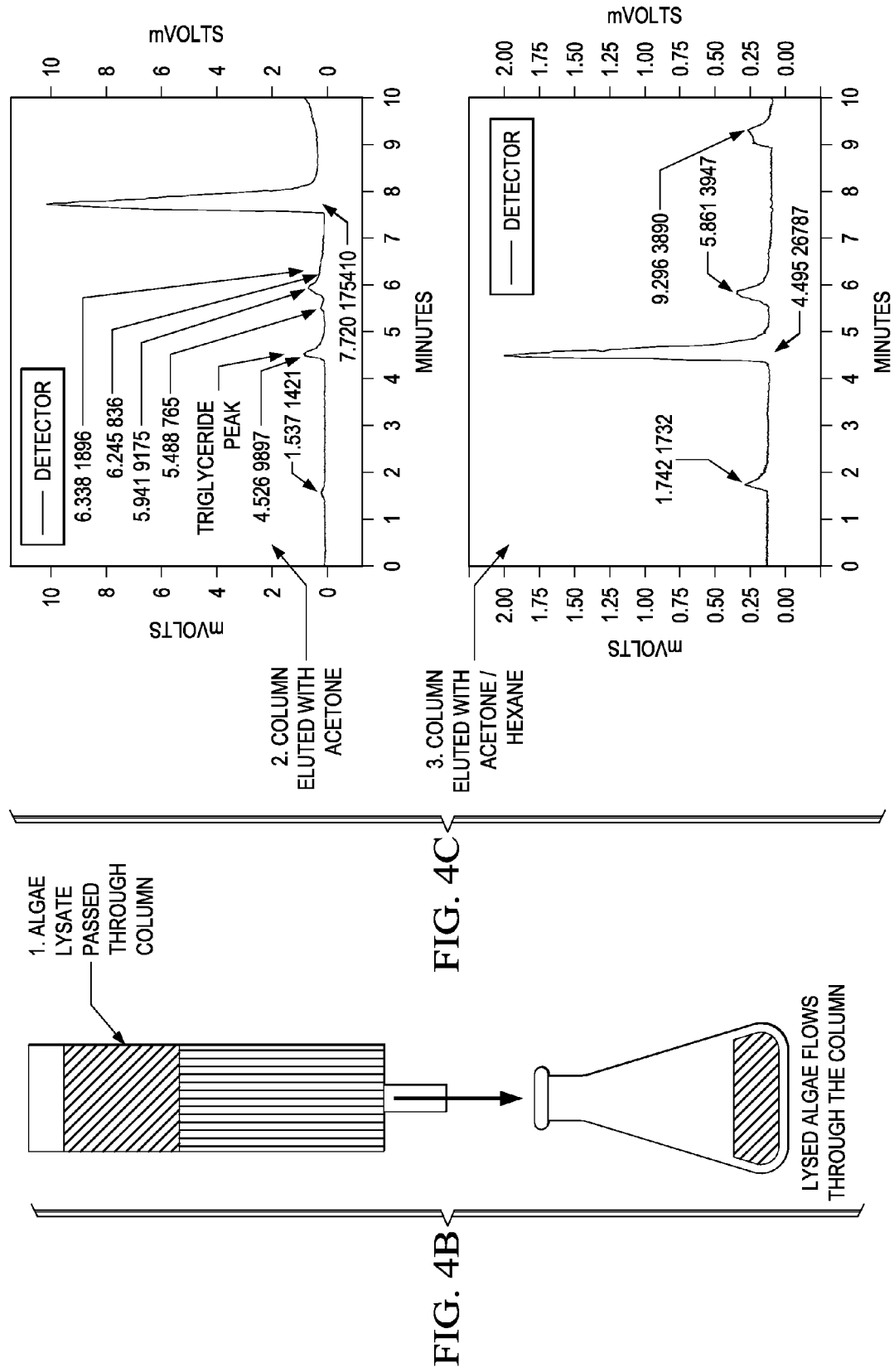

Subsequently the inventors studied the utility of these resins for extracting oils from algae. Visually, it appeared that 100% algae went through resin and drained out the test column (FIG. 4A). Using this approach the inventors first tested the ability of these resins to bind oil present in algae lysates. These lysates were passed over the resin, which was then washed and analyzed for oil content. To remove oil loosely bound to the column the inventors first washed with a polar organic solvent (acetone), and subsequently eluted the oil with hexane. The results (FIGS. 4B and 4C) show that the majority of the oil came off the resin in the hexane wash.

Figure 5A:
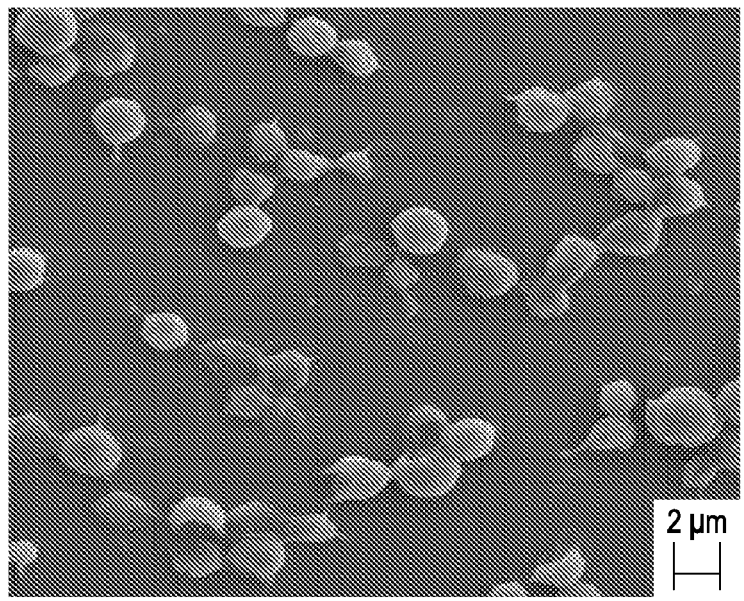
FIGS. 5A and 5B are SEM micrographs showing.
Figure 5B:
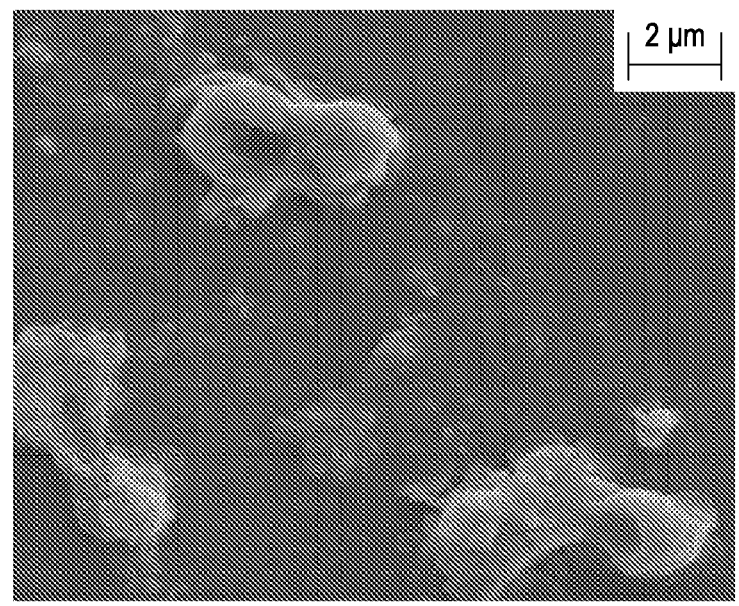

An important feature of these resins is that the algae were found to bind weakly to the column and underwent lysis as they made their way to the column (FIGS. 5A and 5B). In terms of the economics of producing fuels from algae, one of the valuable products is fuel but equally valuable is the remaining algae biomass, which can be used as feed and a source of many valuable biochemicals. However, to be useful, it is important that the algae biomass not be spoiled by introducing toxic solvents or other chemicals as part of the oil extraction process. One of the key virtues of the lipid-binding resins is that algae flow through the column while lipids are retained. The algae biomass passes through untouched by chemicals and subsequent oil elution steps can be carried out after the algae have been removed.

Figure 6:
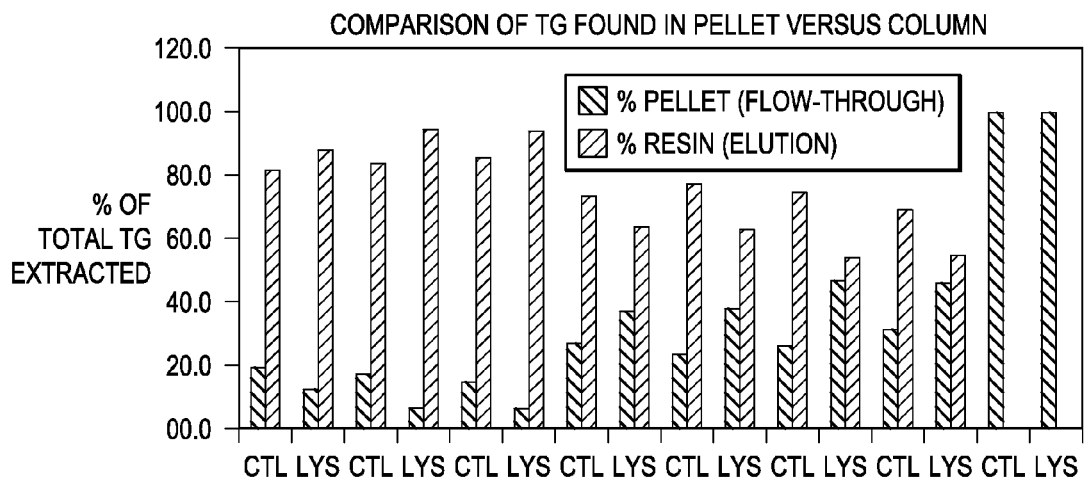
FIG. 6 is a comparison of the resin oil extraction efficiency in lysed and unlysed *Nanochloropsis*. Algae was passed over the resin indicated, washed, and then the oil eluted from the column. Oil (TG) content was analyzed for both flow through and for the eluate. For comparison, oil content was determined for a sample of algae that was not passed through the column (NONE). Algae were either unlysed (CTL) or lysed by freeze/thaw and then sonication (LYS). As can be seen, in many cases, it made little difference if the algae were lysed or not. A number or resins showed the ability to extract 80-90+% of the total triglyceride.
Figure 7A:
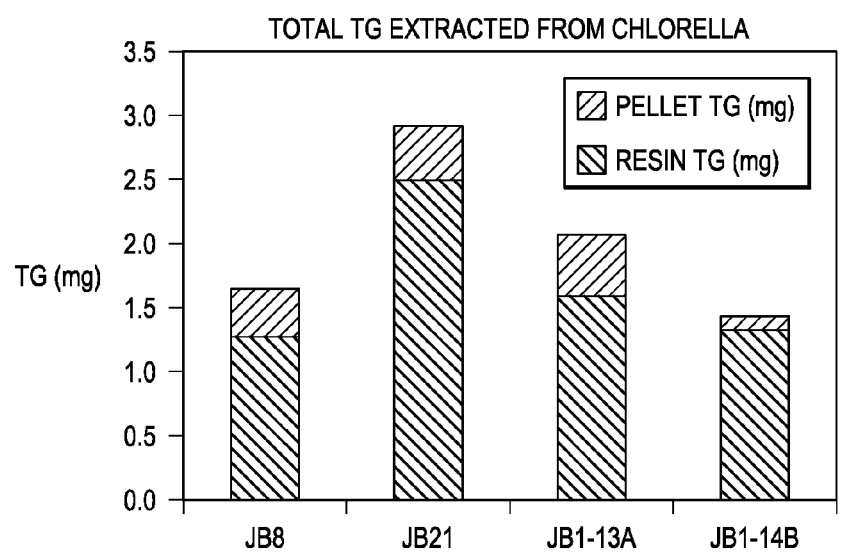
FIGS. 7A and 7B show a comparison of various lipid binding resins for their ability to extract oil from a suspension of *Chlorella* (FIG. 7A) or to extract lipid from an emulsion of vegetable oil (triglyceride) in water (FIG. 7B). Algae were passed through the column and the amount of oil retained on the column as well as the residual oil remaining in the algae was measured by HPLC. The results show that while JB21 extracted the most oil from the algae, JB1-14B was the most effective at binding triglyceride from the emulsion.
Figure 7B:
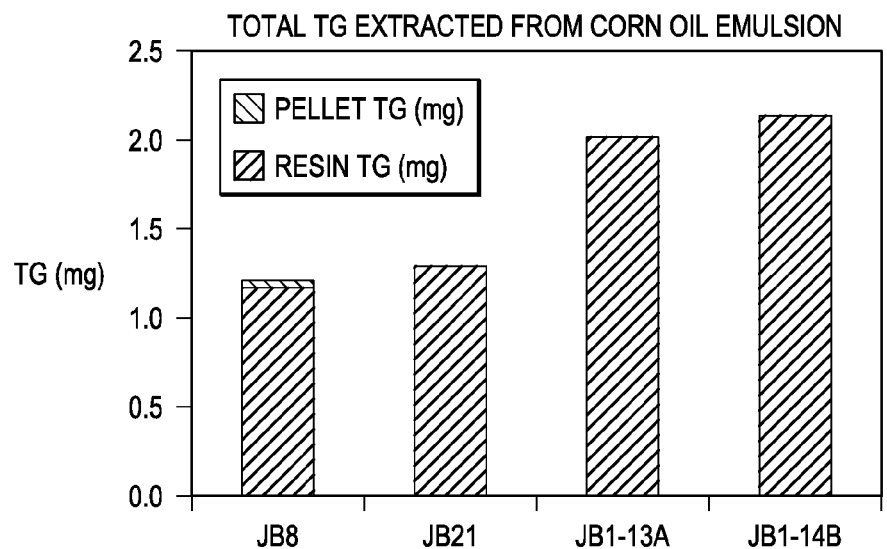
Figure 8:
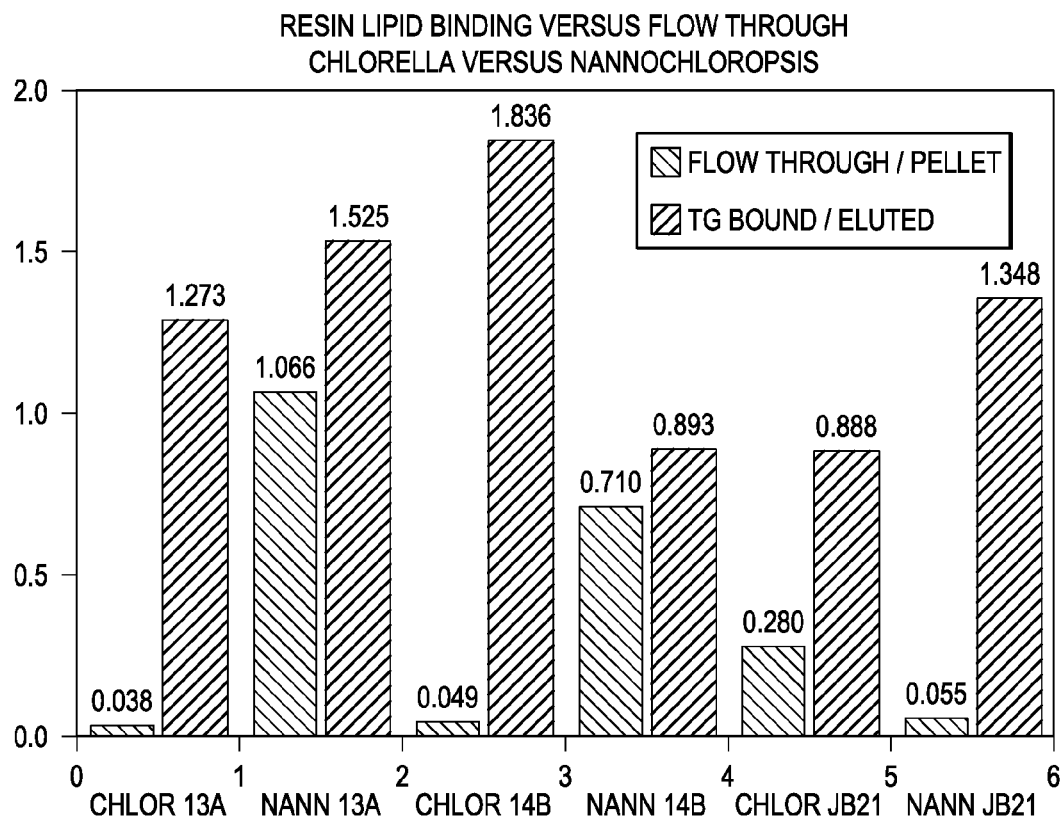
FIG. 8 shows the performance of different resins with two different algae. The light colored bars represent the amount of TG found in the algae flow through whereas the dark bars represent the corresponding amount of lipid eluted off the column after algae was passed through the column. As can be seen JB1-13A and 14B work very well for *Chlorella* whereas JB21 is much better for *Nanochloropsis*.

Characterization of lipid extraction using lipid-binding resins: The inventors tested the ability of the resins to extract oil from lysed as opposed to unlysed algae. The data revealed that for some of the resins, prior lysis did not make a huge difference in the amount of oil recovered from the algae (FIG. 6). Furthermore, while all these resins are more or less hydrophobic and therefore likely to bind lipids, it turned out that their ability to bind triglycerides (a key lipid for biofuel) did not directly correlate with their ability to extract oil from algae (FIGS. 7A and 7B). In FIG. 8 the inventors compared the oil extraction efficiency of several different resins in conjunction with two different algae (*Chlorella* and *Nanochloropsis*). The results indicated that some resins work much better with *Chlorella* whereas other resins are better with *Nanochloropsis*.

An important element in the use of these resins for extracting oil is the amount of solvent it takes to elute the oil off the resin. Were the lipids to bleed off slowly it might take a long time and large volumes of solvent to elute them off the resin. FIG. 9 shows that in fact, the lipids are eluted readily when solvent is passed over the resin.

Certain resins (JB20, 21) bound one algae (*Nanochloropsis*) in a sea water medium even though it has no ionic character. In other words it is not binding the algae by acting as an ion exchange resin. This is an important finding since anion exchange resins based on quaternized ammonium resins do not bind algae effectively in seawater. However, it appears that there are nonionic resins that can accomplish the same goal. A nonionic resin that can bind algae in seawater would greatly extend the usefulness of the approach of the present invention.

Hydrophobic resins can be packed in small columns for use in a rapid algae lipid assay. Algae are passed through the resins and as they pass through, lipids are extracted from the algae. The lipids are then eluted from the resin by use of a solvent. Solvents include hexane or other alkanes, chloroform or other halogenated solvents, ethers such as diethyl ether, acetone or other ketones and aromatic solvents such as benzene or toluene. Once the oil is eluted from the resin, the solvent can be analyzed by analytical methods including HPLC, GC, fluorescence assays for lipids such as Nile Red assay, and other chromatographic methods such as thin layer chromatography.

FIGS. 10A-10D are detailed steps 1000 of how the lipid binding resins 1010 would be used to extract oil. The procedure is conceptually simple. The algae are passed over the column 1002 for some period of time. Once sufficient algae have been passed over the column 1002, the flow of algae would be stopped and the residual algae forced out either with gas pressure or vacuum through inlet 1006. Next, a solvent would be passed over the column 1002 to elute the oil. Here a flow control valve 1014 would divert the solvent into a separate container. Once the elution is complete, residual solvent is forced off the resin, again by pressure or vacuum through inlet 1006. This solvent would then be removed to concentrate the oil. The column in principle should be ready for reuse.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number flowing an eluent through the algae saturated column to elute the algae off the column; and collecting the eluted algae in a receiver connected to the column or the container, wherein the eluted algae comprises the one or more lipid components and the eluent.

2. The method of claim 1, further comprising the steps of:

applying a temperature, a gas pressure, a vacuum or a combination of gas pressure and vacuum, air drying the column or the container or using a combination of other drying techniques to remove any excess eluent from the column or the container;

recycling the eluent for eluting the algae off the column; and repeating the steps of saturating and extracting the one or more lipid components from a subsequent batch of the aqueous algal suspension or the slurry.

TABLE 1

List of lipid binding resins tested.

| Polymer Key | DVB | Styrene | EGDMA | MMA | Hexyl Methacrylate | 2-dimethylamino Ethyl Methacrylate | Triethylene Glycol Dimethacrylate | 2-hydroxyethyl Methacrylate | Template | Surfactant |
|---|---|---|---|---|---|---|---|---|---|---|
| JB8 | 80% | 20% | | | | | | | | |
| JB9 | 80% | 20% | | | | | | | Corn Oil | |
| JB10 | 80% | 20% | | | | | | | Corn Oil | |
| JB11 | 80% | 20% | | | | | | | Methyl laurate | |
| JB12 | 80% | 20% | | | | | | | Glyceryl trioleate | |
| JB20 | | | 80% | 20% | | | | | | |
| JB21 | | | 80% | 20% | | | | | Corn Oil | |
| JB40 | | | 75% | | 15% | 10% | | | Corn Oil | |
| JB1-13A | | | 80% | | 20% | | | | Corn Oil | |
| JB1-13B | | | | | 20% | | 80% | | Corn Oil | |
| JB1-14A | | | 75% | | 15% | | | 10% | | |
| JB1-14B | | | 75% | | 15% | | | 10% | | SPAN 20 |
| JB1-14C | | | 75% | | 15% | | | 10% | | SDS |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 4,341,038: Oil Products from Algae.
U.S. Pat. No. 6,805,800: Method for Recovering Pigments from Algal Cultures.

What is claimed is:

1. A method of extracting one or more lipid components from an aqueous algal suspension or slurry comprising the steps of:

saturating an anion-exchange resin in a column or a container with the algal suspension or slurry;

removing any excess water of liquids from the column or the container by applying a gas pressure, applying a vacuum, air drying the column or the container or using a combination of other drying techniques;

3. The method of claim 1, further comprising the step of converting the eluted algae in the receiver to Fatty Acid Methyl Esters (FAMEs) or a biodiesel.

4. The method of claim 1, wherein the anion-exchange resins comprise a cross-linked polymer backbone with functional groups comprising quarternary ammonium salts, tertiary amines, secondary amines, primary amines, organometallic complexes, any charged species manutactured by corona discharge or plasma ion embedment or any combinations thereof with a replaceable cation.

5. The method of claim 4, wherein the polymer backbone is a selected from the group consisting of styrene, styrene-divinyl benzene, polystyrene, formophenolic, acrylic-divinyl benzene, methacryl-divinyl benzene, functionalized styrene monomers, functionalized acrylic monomers, functionalized metharcylic monomers, acrylamides, methacrylamides, epoxy and acrylic monomers, polypropylene or functionalized polyvinyl chloride polymers.

6. The method of claim 5, wherein the polymer backbone is a divinyl benzene and the functional group is a quarternary ammonium salt.

7. The method of claim 1, wherein the algae are selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella,*

*Monoraphidium, Oocystis, Scenedesmus, Nanochloropsis, Tetraselmis, Chlorella, Dunaliella, Oscillatoria, Synechococcus, Boekelovia, Isochysis, Neochloris oleoabundans,* and *Pleurochysis.*

8. The method of claim 1, wherein the anion exchange resin is an electrostatically charged polyethylene.

9. The method of claim 1, wherein the eluent comprises methanol acidified with sulfuric acid or methanol with sodium hydroxide, potassium hydroxide, sodium ethoxide or sodium methoxide.

10. The method of claim 1, wherein the algae is a *Chlorella.*

11. The method of claim 1, wherein the algae is a *Nanochloropsis.*

12. A method of extracting one or more lipid components from an aqueous algal suspension or slurry of *Chlorella, Nanochloropsis* or both using an anion exchange resin in a column or a container, wherein the anion exchange resin comprises a divinylbenzene or other crosslinked polymer backbones with an attached quarternary ammonium salt functional group comprising the steps of:
  saturating the anion exchange column or container with the *Chlorella, Nanochloropsis* or both wherein the saturation of the column is determined by a presence of the *Chlorella, Nanochloropsis* or both in a column effluent detected by an optical sensor attached to the base of the column or the container;
  removing any excess water of liquids from the column or the container by applying a gas pressure, applying a vacuum, air drying the column or the container or using a combination of other drying techniques;
  flowing an eluent comprising methanol acidified with sulfuric acid through the algae saturated column to elute the algae off the column or the container; and
  collecting the eluted *Chlorella, Nanochloropsis* algae or both in a receiver connected to the column or the container, wherein the eluted algae comprises the one or more lipid components and the eluent.

13. The method of claim 12, further comprising the steps of:
  applying a temperature, a gas pressure, a vacuum, a combination of gas pressure and vacuum, air drying the column or the container or using a combination of other drying techniques to remove any excess eluent from the column or the container;
  recycling the eluent comprising methanol acidified with sulfuric acid to elute the algae off the column of the container, wherein the sulfuric acid is added to the eluent before recycling; and
  repeating the steps of saturating and extracting the one or more lipid components from a subsequent batch of aqueous algal suspension or slurry of *Chlorella* or *Nanochloropsis.*

14. The method of claim 12, wherein the anion exchange resin is an electrostatically charged polyethylene.

15. The method of claim 12, further comprising the step of converting the eluted *Chlorella Nanochloropsis* algae or both in the receiver to Fatty Acid Methyl Esters (FAMEs) or a biodiesel.

16. A method of extracting one or more lipid components from an aqueous algal suspension or slurry comprising the steps of:
  saturating a lipid binding column or a container comprising a lipid binding hydrophobic resin with the algae;
  stopping the flow of the algae at the saturation point of the column or the container;
  applying a gas pressure or a vacuum to the column or the container to remove any residual algae from the column or the container;
  passing a solvent through the column or the container to extract the bound one or more lipid components and the oils, wherein the solvents are selected from the group consisting of hexane or other alkanes, chloroform or other halogenated solvents, ethers, ketones, and other aromatic solvents;
  collecting the solvent comprising the dissolved one or more lipid components and the oil in a separate receiver; and
  removing the solvent to obtain a concentrate comprising the one or more lipid components and the oil.

17. The method of claim 16, further comprising the step of analyzing the eluted solvent comprising the dissolved lipid components by one or more analytical techniques selected from the group consisting of high pressure liquid chromatography (HPLC), gas chromatography (GC), fluorescence, thin-layer chromatography (TLC), and other chromatographic methods.

18. The method of claim 16, further comprising the steps of:
  removing any excess water of liquids from the column or the container by applying a gas pressure, applying a vacuum, air drying the column or the container, or using a combination of other drying techniques; and
  repeating the steps of saturating and extracting the one or more lipid components from a subsequent batch of aqueous algal suspension or slurry.

19. The method of claim 16, further comprising the step of converting the concentrated lipid components and oil in the receiver to Fatty Acid Methyl Esters (FAMEs) or a biodiesel.

20. The method of claim 16, wherein the lipid binding resin comprises a polymer backbone, wherein the polymer backbone selected from the group consisting of styrene, divinyl benzene, styrene-divinyl benzene, polystyrene, formophenolic, acrylic-divinyl benzene, methacryl-divinyl benzene, functionalized styrene monomers functionalized acrylic monomers, functionalized metharcylic monomers, acrylamides, methacrylamides, epoxy and acrylic monomers or polypropylene or functionalized polyvinyl chloride polymers, wherein one or more copolymerizing monomers with various hydrophilic or hydrophobic functional groups are attached to the polymer backbone.

21. The method of claim 16, wherein the algae are selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis, Neochloris oleoabundans,* and *Pleurochysis.*

22. The method of claim 16, wherein the solvent comprises acetone, heptane, hexane, pentane, benzene, toluene, tetrahydrofuran, diethy ether, ethyl acetate or mixtures thereof.

23. The method of claim 16, wherein the algae is a *Chlorella.*

24. The method of claim 16, wherein the algae is a *Nanochloropsis.*

25. The method of claim 20, wherein the polymer backbone is a crosslinked divinyl benzene or other crosslinked monomers, wherein the polymer backbone is at least 2% cross-linked.

26. A method of extracting one or more lipid components from an aqueous algal suspension or slurry of *Chlorella, Nanochloropsis* or both comprising the steps of:
   saturating a lipid binding resin column or a container comprising a cross-linked divinyl benzene or other crosslinked polymers with the suspension or slurry of the *Chlorella, Nanochloropsis* or both;
   applying a temperature, a gas pressure, a vacuum or a combination of gas pressure and vacuum to the column or the container to remove any residual algae from the column;
   passing hexane or other non-polar organic solvent through the column or the container to extract the bound one or more lipid components and the oils;
   collecting the hexane or the non-polar organic solvent comprising the dissolved one or more lipid components and the oil in a separate receiver; and
   removing the hexane or the non-polar organic solvent to obtain a concentrate comprising the one or more lipid components and the oil.

27. The method of claim 26, further comprising the step of analyzing the hexane or the non-polar organic solvent comprising the dissolved one or more lipid components by one or more analytical techniques selected from the group consisting of high pressure liquid chromatography (HPLC), gas chromatography (GC), fluorescence, thin-layer chromatography (TLC), and other chromatographic methods.

28. The method of claim 26, further comprising the steps of:
   applying a temperature, a gas pressure, a vacuum, a combination of gas pressure and vacuum, air drying the column or the container, or using a combination of other drying techniques to remove any excess hexane or other solvent from the column or the container; and repeating the steps of saturating and extracting the one or more lipid components from a subsequent batch of aqueous algal suspension or slurry of *Chlorella, Nanochloropsis* or both.

29. The method of claim 26, further comprising the step of converting the concentrated lipid components and oil in the receiver to Fatty Acid Methyl Esters (FAMEs) or a biodiesel by transesterification, wherein the transesterification is catalyzed by an acid or a base.

* * * * *